United States Patent [19]

Halkyard

[11] 4,446,967
[45] May 8, 1984

[54] GERMICIDE SLEEVE FOR DENTAL AND MEDICAL INSTRUMENTS

[76] Inventor: Douglas R. Halkyard, 4300 Sandridge Rd., Morris, Ill. 60450

[21] Appl. No.: 376,061

[22] Filed: May 7, 1982

[51] Int. Cl.³ .............................................. B65D 83/10
[52] U.S. Cl. ................................... 206/368; 206/363; 206/364; 206/306; 206/365
[58] Field of Search ............... 206/363, 364, 365, 368, 206/306, 523, 592, 210, 229

[56] References Cited

U.S. PATENT DOCUMENTS

| | | | |
|---|---|---|---|
| 2,400,722 | 5/1946 | Swan | 206/365 |
| 2,421,495 | 6/1947 | Green | 206/365 |
| 2,803,252 | 8/1957 | Bloome | 206/210 |
| 3,270,743 | 9/1966 | Gingras | 206/210 |
| 3,434,473 | 3/1969 | Smith | 206/365 |
| 3,637,072 | 1/1972 | Narusawa et al. | 206/365 |
| 3,693,783 | 9/1972 | Hart | 206/210 |
| 4,113,090 | 9/1978 | Carstens | 206/365 |

FOREIGN PATENT DOCUMENTS 1396464  6/1975  United Kingdom ................ 206/365

*Primary Examiner*—Joseph Man-Fu Moy
*Attorney, Agent, or Firm*—Ernest Kettelson

[57] ABSTRACT

A germicide sleeve for dental and medical instruments comprising a flexible non-permeable outer sleeve wall of plastic or the like, the sleeve being closed at one end, the inner wall lined with a compressible absorbent material such as foam rubber surrounding an elongated central cavity or bore which extends the length of the sleeve and opens at an open end thereof to receive the working portion of a dental or medical instrument therein, the absorbent material being impregnated with a germicide solution to disinfect the instrument while stored therein, the compressible absorbent material which completely surrounds the central bore or cavity also serving as a protective cushion for the instrument stored therein while awaiting use. The germicide sleeve is disposable after its first use, and the instrument may be placed in a new germicide sleeve after each use of the instrument. The open end of the germicide sleeve is covered by a breakable seal prior to use. The germicide solution may be injected into the sleeve to impregnate the absorbent material after the seal has been broken and just prior to placing a dental or medical instrument therein. In this way, the full active life of the germicide is available for disinfection of the instrument while stored therein, and a germicide injector having an elongated nozzle with spaced apart openings along its side wall for insertion into the central bore of the sleeve to impregnate the absorbent material is part of this invention.

11 Claims, 4 Drawing Figures

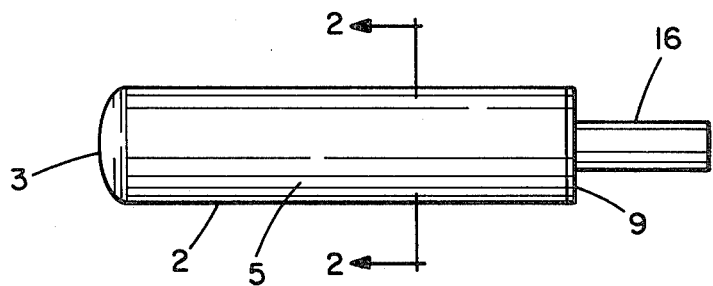
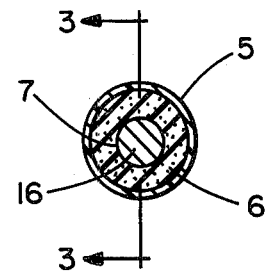
FIG. 1
FIG. 2
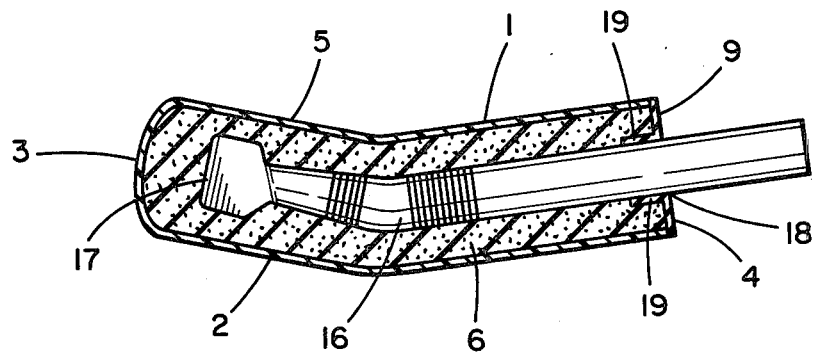
FIG. 3
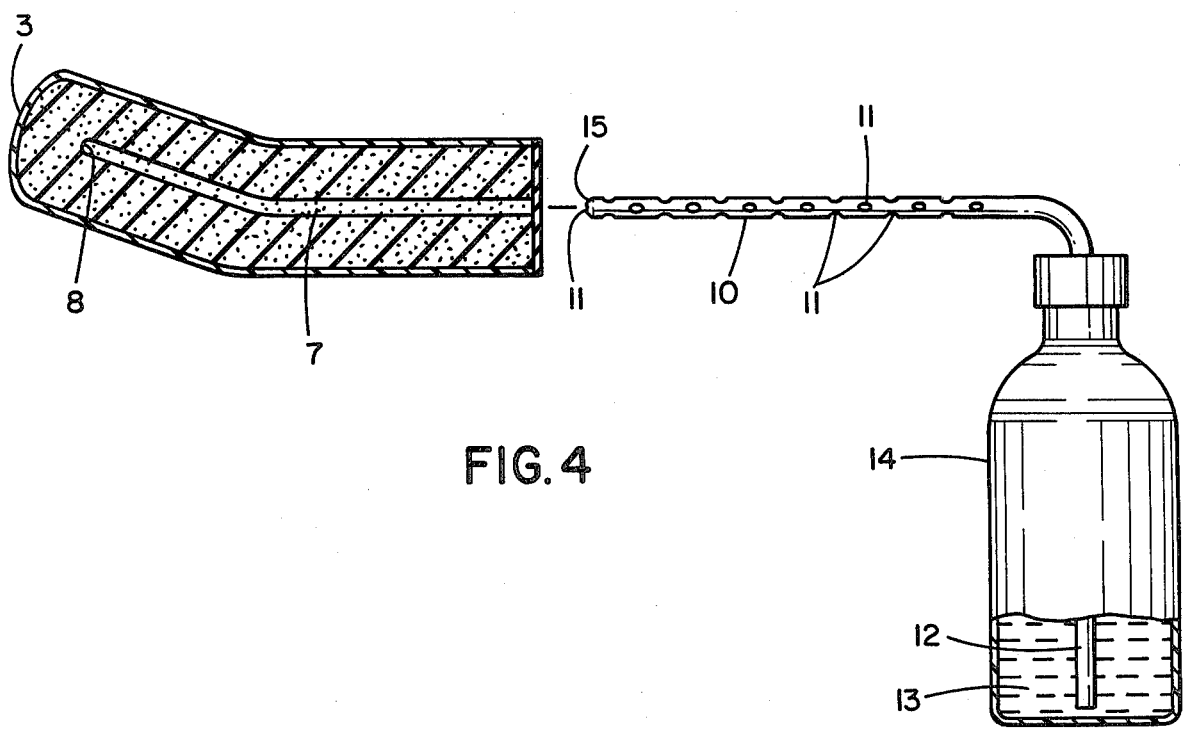
FIG. 4

GERMICIDE SLEEVE FOR DENTAL AND MEDICAL INSTRUMENTS

BACKGROUND OF THE INVENTION

This invention relates to the field of devices for disinfecting or cleansing dental and medical instruments of germs or bacteria prior to use on patients, or for keeping them in a germ-free or bacteria-free environment prior to use, and in particular to such devices which are disposable after their first use.

Prior art devices of this kind include sheaths or sleeves which have pockets that are more or less airtight to prevent entrance of germs or bacteria in which the instrument is packaged when new, or originally sterilized or disinfected. Devices of this kind are illustrated and disclosed in U.S. Pat. Nos. 4,178,735 and 3,331,499.

Other prior art devices in this general field include disposal pads for sharp instruments usable during surgery, in which the instruments are placed on a foam pad lining of a non-porous outer layer, the foam lining being impregnated with an adhesive substance to keep the instruments in place conveniently ready as needed by the surgeon during an operation, as disclosed in U.S. Pat. No. 4,076,882.

Various other devices for disinfecting or sterilizing dental and medical instruments known to the prior art include those disclosed in U.S. Pat. No. 3,270,743 (a hypodermic syringe in a cylindrical container having a wad of antiseptic impregnated cotton in the bottom to contact the needle end of the instrument while in the container), U.S. Pat. No. 1,647,637 (a reusable sterilizer having absorbent cotton in the bottom saturated with formaldehyde to disinfect dental handpieces), U.S. Pat. No. 1,496,426 (another reusable sterilizer for dental handpieces having a wad of cotton at one end impregnated with a disinfectant), and U.S. Pat. No. 1,330,460 (a box-like container having a wad of cotton saturated with formaldehyde to disinfect a vibrating device, this one also reusable).

Another prior art patent, U.S. Pat. No. 3,633,758 discloses tubular sleeves to receive a medical instrument, a catheter in this case, the sleeves conforming to the outer shape of the instrument, but there is no suggestion of lining the inner wall of the sleeves with a foam material which can be impregnated with a germicide to disinfect the instrument while it is awaiting use, after which the tubular sleeve is discarded.

None of the prior art devices provide a convenient disposable means of disinfecting a dental or medical instrument while being stored in between uses of the instrument, means which is flexible having a foam lined interior capable of receiving instruments of various exterior shapes and closely contacting the entire exterior surface areas of such instruments received therein, the foam lining being impregnated with fresh germicide material to disinfect the entire exterior surface areas of the instruments while remaining in the sleeve awaiting use.

SUMMARY OF THE INVENTION

It is an object of this invention to provide a flexible germicide sleeve for dental and medical instruments having a foam lined interior wall, the foam lining being impregnated with a germicide to disinfect a dental or medical instrument received therein, such germicide impregnated foam material contacting the entire exterior surface areas of such dental or medical instrument.

It is an object of the invention to provide a flexible sheet germicide sleeve for dental and medical instruments having a foam lined interior wall capable of conforming to the exterior shape of a variety of dental and medical instruments.

It is an object of the invention to provide a germicide sleeve for dental and medical instruments which is disposable after its first use.

It is an object of this invention to provide a germicide sleeve for dental and medical instruments having a cavity therein surrounded by compressible absorbent material to receive and closely contact all exterior surface areas of dental or medical instruments inserted therein, such compressible absorbent material being impregnated with a germicide just prior to inserting a dental or medical instrument therein.

It is an object of this invention to provide injector means to impregnate the absorbent lining of the inner wall of a germicide sleeve with a germicide, such injector means including an elongated nozzle conforming to the length and diameter of the central bore of said sleeve, such elongated nozzle having spaced apart perforations therein to permit a flow of germicide therethrough when directed into and through said nozzle from a source of supply of said germicide.

It is an object of this invention to provide a flexible germicide sleeve for dental and medical instruments having compressible absorbent material around its inner wall to cushion and protect a dental or medical instrument received therein while at the same time disinfecting such instrument.

BRIEF DESCRIPTION OF THE DRAWING

FIG. 1 is a side elevation view of a germicide sleeve for dental and medical instruments in accordance with this invention and an instrument received therein with a portion extending outwardly thereof.

FIG. 2 is a section view taken on line 2—2 of FIG. 1.

FIG. 3 is a section view taken on line 3—3 of FIG. 2.

FIG. 4 is a section view similar to FIG. 3 but with the instrument removed, and including a germicide impregnating nozzle positioned for entry into the central bore of the germicide sleeve, the nozzle connected to a supply of germicide solution.

DESCRIPTION OF PREFERRED EMBODIMENT

A germicide sleeve 1 for dental and medical instruments comprising an elongated sleeve 2 having a closed end wall 3 and an opposite open end wall 4. The elongated sleeve 2 includes a flexible outer wall 5 of nonpermeable material such as plastic or the like. The closed end wall 3 may also be of such flexible nonpermeable material. The inner surface of the flexible outer wall 5 has a relatively thick layer of compressible absorbent material 6, such as foam rubber or various types of plastic foam material connected thereto throughout its entire length and around its entire inner periphery, defining a relatively small diameter central bore 7 extending for substantially the entire length of the sleeve 2 and opening to the open end wall 4. The inner surface of the closed end wall 3 also has a relatively thick layer of such compressible absorbent material 6 connected thereto, the inner end 8 of the central bore 7 terminating at such layer of compressible absorbent material connected to the inner surface of the closed end wall 3.

The open end wall 4 has a breakable seal 9 of plastic or other non-permeable material, but which may be broken or punctured by an object forced against it in the direction toward the central bore 7. The seal 9 may be adhered to the peripheral edge of the outer wall 5 at and around its open end wall 4, by heat sealing or by an appropriate adhesive. The seal 9 is thin enough to be punctured by a tool or object pressed against it from the outside. The seal 9 is also resilient or elastic whereby it tends to frictionally and elastically adhered to the side wall of the tool or object as it passes through after such puncture, the portions of the seal 9 elastically gripping around the side wall of the tool or object being carried inwardly of said central bore 7 a short distance as said tool or object is moved inwardly into said central bore 7, thereby maintaining a seal around the side wall of the tool or object.

When the sleeve 1 of this invention is manufactured with the seal 9 in place to completely close the open end wall 4, the compressible absorbent material 6 around the inner surface of the sleeve wall 5 has not as yet been impregnated with germicide in one form of this invention. The germicide is injected later, just before the sleeve is to be used with a dental or medical instrument. The reason for this is that most germicide solutions remain fully active after being exposed for a period of about 30 days. If the germicide is injected into the absorbent material 6 at the time of manufacture, it may lose its full effectiveness by the time it is sold to a dentist or doctor for use in disinfecting their instruments unless additional measures are taken.

Therefore, in accordance with this invention, injection means are provided to inject germicide into the absorbent material 6 just prior to the time the dentist or doctor is ready to use one of the sleeves 1 to place an instrument in for safe storage and at the same time disinfection of the instrument until such time as it will be used again. One form of such injection means is an elongated nozzle 10 having a plurality of spaced apart apertures 11, connected by a tube 12 to a supply source of germicide solution 13. As shown in the drawing, the germicide solution 13 is contained in a squeezable container 14 which may be hand squeezed to force a quantity of germicide solution 13 out of the container 14, through the tube 12 and into nozzle 10.

The free end 15 of the nozzle 10 is rounded or tapered to more easily puncture the seal 9 in its center when held thereagainst and pressure applied in the direction toward the central bore 7. When the seal 9 punctures, the nozzle 10 then passes into the central bore 7 extending substantially the entire length of the sleeve 2. The length of the nozzle 10 corresponds substantially to the length of the central bore 7. When fully inserted, the spaced apart apertures 11 along the nozzle 10 and around the nozzle 10, as well as in the free end 15 of nozzle 10, are facing corresponding portions of the compressible absorbent material 6 throughout its entire length and around its entire circumference. At such time, a quantity of germicide solution 13 is forced into the nozzle 10 and out the plurality of apertures 11 to completely impregnate the inner wall layer of compressible absorbent material 6 throughout its entire length. The nozzle 10 is then withdrawn from the central bore 7.

A dental or medical instrument of corresponding size to that of the particular sleeve chosen, such as a dental air rotor 16, is then placed with its head portion 17 against the central portion of the outer face of the seal 9 and pushed inwardly until the seal 9 (which has already been punctured by the nozzle 10 forming a relatively small opening through the seal 9) punctures further to allow the relatively larger size head 17 of the instrument or tool 16 to pass and enter the central bore 7. As the head 17 passes into the central bore 7, it pushes and compresses the absorbent material 6 radially outwardly toward the side wall 5 thus enlarging the diameter of the central bore 7 as it goes and causing the compressible absorbent material to compress against all parts of the exterior surface area of the tool 16 received in the central bore 7. In this way, all parts of the exterior surface area are contacted by the compressible absorbent material which has now been impregnated with a germicide solution 13. The compressing action of the tool 16 entering the central bore 7, enlarging it as it proceeds and compressing the absorbent material 6 in a radially outward direction, provides a squeezing action which squeezes germicide solution 13 onto and around the tool 16 thoroughly contacting all exterior surface areas thereof with germicide solution 13 to thoroughly disinfect all parts thereof.

The elastic seal 9, as its puncute hole 18 becomes larger when the head 17 of tool 16 breaks through, has portions 19 thereof which elastically grip and surround the puncture hole 18 and which are pushed inwardly as the tool 16 is pushed inwardly to form and provide a seal around the portion of the body of tool 16 adjacent to such portions 19 of seal 9. This seal protects the interior of the sleeve 1 from exterior contaminants, and at the same time prevents leakage of germicide solution 13 from the interior to the exterior.

The compressible absorbent material 6 serves a dual purpose, acting as a protective cushion which completely surrounds the instrument or tool 16 received within the central bore 7 of the sleeve 1 in addition to providing an intimate contact source of germicide solution 13 to all parts of the exterior surface area of the tool 16 received therein.

Germicide solutions 13 which may be used with this invention include glutaraldehyde solutions such as Sporicidin which have been recommended as germicides which are suitable for use in dentistry by the Council on Dental Therapeutics. These germicide solutions may be used in accordance with this invention to impregnate the absorbent material 6 as described above. However, identifying certain of the germicide solutions which may be used does not exclude the use of other germicide solutions.

The shape, size and configuration of the germicide sleeves 1 in accordance with this invention may vary depending on the shape, size and configuration of the dental and medical instruments with which they are to be used. In general, the sleeves 1 may be elongated and cylindrical in cross-sectional configurations since they are flexible and can readily conform to the shape and cross-sectional configuration of many different instruments as they are pushed into the central bore 7. The diameter of the central bore 7 when the surrounding layer of compressible absorbent material 6 is in its expanded or uncompressed state is preferably several times smaller than the diameter or cross-section of the instrument or tool 16 that is to be inserted therein. Since the sleeves 1 may be elongated and cylindrical in shape for use with many different dental and medical instruments, they have a universal character to them whereby it is not necessary to order and have on hand a wide variety of germicide sleeves separately shaped for use with separate individual types of instruments. The primary variant will be diameter size and longitudinal length, depending on the cross-sectional dimension of the instrument with which the sleeve is to be used and its length.

The sleeves 1 are disposable and are to be discarded after their first use, that is after a dental or medical instrument has been stored therein for a given period of time in between uses. When the instrument is withdrawn from the sleeve 1 for use of the instrument, that sleeve 1 is discarded. When use of this instrument has been completed and it is ready to be stored again, a new unused sleeve 1 is taken, a quantity of germicide injected therein to impregnate its absorbent layer of material 6 as described above, and the instrument inserted through the puncture hole 18 of the seal 9 into the central bore 7 until fully inserted into the central bore, with the inwardly extending elastic edge portions 19 of seal 9 surrounding the puncture hole 18 sealingly bearing against that portion of the body of the instrument or tool 16 adjacent thereto to seal in the germicide solution 13 and seal out contaminants from the exterior.

The layer of compressible absorbent material 6 is sufficiently thick to provide good cushioning protection for a dental or medical instrument in the central bore 7, so as to prevent or minimize physical damage to the instrument if accidentally dropped on the floor or if other impact type of accident occurs. The thickness of the layer of compressible material 6 may be up to about one-half the cross-sectional dimension of the tubular sleeve 1 or just slightly less, so when placed around the inner surface of the peripheral wall 5, the layer of compressible material 6 nearly fills the space within the confines of the peripheral wall 5 leaving only a relatively small diameter central bore 7, that is when expandable central bore 7 is in its unexpanded state and the layer of compressible material 6 is not compressed. The diameter of central bore 7 in its unexpected state is shorter in dimension than the thickness of the layer of compressible material 6 around the inner surface of the wall 5 when not compressed. Thus, the germicide sleeves 1 in accordance with this invention not only provide protection against germs and bacteria by disinfecting instruments placed therein, but they also provide protection against physical damage from impact against solid objects such as dropping on the floor, hitting against a table or cabinet, dropping a book or other solid object on the instrument encased in the protective sleeve 1, and the like, by virtue of the relatively thick layer of cushioning compressible material 6 which completely surrounds the central bore 7 in which the instrument is placed.

The germicide sleeve or enclosure in accordance with this invention has been described herein as being used for dental and medical instruments. It can of course be used for all types of instruments or implements which require disinfecting, or used in any way in the care and treatment of living beings, including those used by beauticians in beauty shops, manicurists, barbers and the like. Surgical instruments are included in the general terms "dental and medical instruments" as used in this case, the germicide enclosure in accordance with this invention being particularly well adapted for use with surgical instruments to store and disinfect them between uses. The general term "dental and medical instruments" as used herein also includes instruments used by veterinarians in the care and treatment of animals, such veterinarian's instruments capable of being stored and disinfected in the germicide sleeves or enclosures of this invention.

I claim:

1. A germicide enclosure to disinfect instruments used in the care and treatment of living beings, comprising an elongated enclosure having an open end, an outer wall of flexible sheet material extending from said open end to the opposite end of said elongated enclosure, said flexible sheet material comprising material having the characteristic of being able to readily conform to the shape of irregularly shaped instruments including those which have a bent shape wherein said flexible sheet material correspondingly bends to conform to such shape when such instrument is received in said sleeve, an inner wall of compressible absorbent material, an expandable diameter central bore bounded by said inner wall of compressible absorbent material and opening to said open end of said elongated enclosure, said expandable diameter central bore being expandable throughout its longitudinal dimension to conform at all points to the exterior configuration and dimension of a said instrument received therein and contractable to the original diameter of said central bore when said instrument is removed therefrom, said inner wall of compressible absorbent material being impregnable with a germicide solution, said inner wall of compressible absorbent material being compressible to permit expansion of said expandable diameter central bore sufficiently to receive instruments having a cross-sectional dimension substantially greater than that of a hypodermic needle and expandable back to its original thickness when not compressed to enable return of said expandable diameter bore to its original dimension, and sealing means to seal said open end to prevent leakage of said solution therethrough.

2. A germicide enclosure to disinfect instruments as set forth in claim 1, wherein said flexible sheet material of said outer wall is non-permeable, said expandable central bore being expandable in diameter sufficiently to receive instruments therein having a cross-sectional dimension as large as that of a dental air rotor.

3. A germicide enclosure to disinfect instruments as set forth in claim 1, wherein said inner wall of compressible absorbent material extends throughout the entire length of said elongated enclosure adjacent the inner surface of said outer wall from said open end to the opposite end of said elongated enclosure, said compressible absorbent material comprising a foam substance, said central bore extending from said open end for substantially the length of said elongated enclosure terminating at a point near and inwardly of said opposite end.

4. A germicide enclosure to disinfect instruments as set forth in claim 1, wherein said expandable diameter central bore is in its unexpanded condition and said inner wall of compressible absorbent material is not compressed, the diameter of said central bore is then substantially smaller than the cross-sectional dimension of the said instrument with which it is to be used.

5. A germicide enclosure to disinfect instruments as set forth in claim 3, including impregnating means to impregnate said inner wall of compressible absorbent material with a germicide solution.

6. A germicide enclosure to disinfect instruments as set forth in claim 5, wherein said impregnating means includes an elongated cylindrical nozzle having a diameter corresponding to that of said central bore in its unexpanded state and a longitudinal dimension corresponding to the longitudinal dimension of said central bore, a plurality of apertures in spaced apart relationship along and around said elongated cylindrical nozzle, germicide storage means, conduit means connecting said nozzle to said germicide storage means, and flow means to flow germicide solution from said storage means to said nozzle and out through said plurality of apertures to impregnate said inner wall of compressible absorbent material when said nozzle is inserted in said central bore.

7. A germicide enclosure to disinfect instruments as set forth in claim 6, wherein said sealing means includes a resilient, pierceable sealing member across said open end, said nozzle includes forwardly extending free end means to pierce said pierceable sealing member when pressed thereagainst in the direction to enter said central bore.

8. A germicide enclosure to disinfect instruments as set forth in claim 7, including an elongated instrument for use in said care and treatment of living beings, said instrument having a cross-sectional dimension substantially larger than said expandable central bore in its unexpanded state, said instrument including a working head portion at one end, said sealing member being pierceable by said head portion when pressed thereagainst in the direction to enter said central bore to provide a puncture hole in said sealing member, elastic edge portions of said sealing member around said puncture hole to elastically grip the peripheral side portions of said instrument as it passes through said puncture hole and into said expandable central bore, said elastic edge portions which elastically grip said peripheral side wall portions of said instrument extending inwardly from said open end wall of said sleeve a short distance when said instrument is inserted in said central bore and providing a seal around said peripheral side wall portions of said instrument to seal in said germicide solution and seal out external contaminants.

9. A germicide enclosure to disinfect instruments as set forth in claim 6, wherein said germicide storage means includes a flexible squeezable container, said flow means to flow germicide solution from storage means to said nozzle includes said squeezable container whereby germicide solution therein is forced out through said conduit means to said nozzle inserted in said central bore and out through said plurality of apertures of said nozzle to impregnate said inner wall of compressible absorbent material when said squeezable container is squeezed.

10. A germicide enclosure to disinfect instruments as set forth in claim 8, wherein said instrument is a dental air rotor.

11. A germicide enclosure to disinfect instruments as set forth in claim 1, wherein said outer wall of flexible sheet material and said inner wall of compressible absorbent material comprise one time use materials, said germicide enclosure being intended for disposal after a one time use.

* * * * *